United States Patent
Reiderman

(10) Patent No.: US 9,482,778 B2
(45) Date of Patent: Nov. 1, 2016

(54) ULTRA-SLIM NUCLEAR MAGNETIC RESONANCE TOOL FOR OIL WELL LOGGING

(71) Applicant: Arcady Reiderman, Katy, TX (US)

(72) Inventor: Arcady Reiderman, Katy, TX (US)

(*) Notice: Subject to any disclaimer, the term of this patent is extended or adjusted under 35 U.S.C. 154(b) by 334 days.

(21) Appl. No.: 14/164,265

(22) Filed: Jan. 27, 2014

(65) Prior Publication Data

US 2015/0212225 A1 Jul. 30, 2015

(51) Int. Cl.
*G01V 3/32* (2006.01)
*E21B 47/12* (2012.01)
*G01N 24/08* (2006.01)
*G01R 33/38* (2006.01)
*G01R 33/381* (2006.01)
*G01R 33/383* (2006.01)
*G01R 33/421* (2006.01)

(52) U.S. Cl.
CPC .............. *G01V 3/32* (2013.01); *E21B 47/122* (2013.01); *G01N 24/081* (2013.01); *G01R 33/3808* (2013.01); *G01R 33/381* (2013.01); *G01R 33/383* (2013.01); *G01R 33/421* (2013.01)

(58) Field of Classification Search
CPC .... G01V 3/32; G01N 24/081; E21B 47/122; E21B 47/01; E21B 47/00; E21B 47/02216; E21B 47/044; E21B 47/082; E21B 47/0905; E21B 47/1015; G01R 33/3808; G01R 33/381; G01R 33/383; G01R 33/421
See application file for complete search history.

(56) References Cited

U.S. PATENT DOCUMENTS

| | | | | | |
|---|---|---|---|---|---|
| 5,712,566 | A | * | 1/1998 | Taicher | G01N 24/081 324/303 |
| 6,125,934 | A | * | 10/2000 | Lenn | E21B 47/1015 166/250.07 |
| 6,585,043 | B1 | * | 7/2003 | Murray | E21B 17/1057 166/241.3 |
| 7,069,775 | B2 | * | 7/2006 | Fredette | E21B 47/082 73/152.17 |
| 8,044,662 | B2 | * | 10/2011 | Fransson | G01N 24/08 324/303 |
| 8,103,135 | B2 | * | 1/2012 | Head | E21B 17/023 385/12 |
| 8,443,915 | B2 | * | 5/2013 | Storm, Jr. | E21B 10/62 175/40 |
| 9,074,436 | B2 | * | 7/2015 | Runia | E21B 10/62 |
| 2005/0030021 | A1 | * | 2/2005 | Prammer | G01V 3/32 324/303 |
| 2010/0277167 | A1 | * | 11/2010 | Romero | G01N 24/081 324/303 |

* cited by examiner

*Primary Examiner* — Michael Zarroli
(74) *Attorney, Agent, or Firm* — Pierson IP, PLLC

(57) ABSTRACT

NMR properties of earth formations are determined using a logging device movable in a borehole. The logging device includes a magnet assembly to generate a static magnetic field and an antenna expandable from the surface of the magnet assembly into the borehole toward the borehole wall to increase the magnetic dipole moment of the antenna. The logging device can be lowered or raised through a drill pipe with the magnet assembly being configured to generate no magnetic field while the device is conveyed within the drill pipe. The logging device may also include a side-looking sensor to acquire fast relaxation component of the NMR signals.

16 Claims, 6 Drawing Sheets

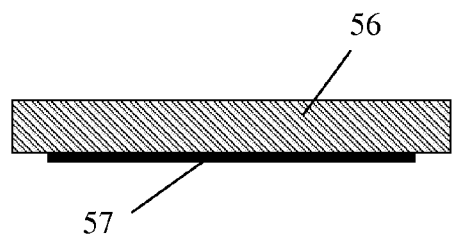
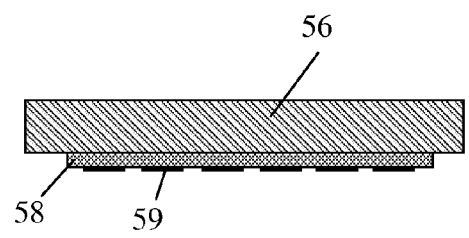
FIG. 4A                FIG. 4B
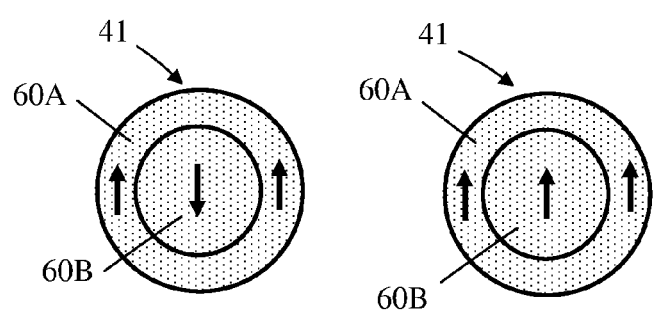
FIG. 5A        FIG. 5B        FIG. 5C

ULTRA-SLIM NUCLEAR MAGNETIC RESONANCE TOOL FOR OIL WELL LOGGING

STATEMENT REGARDING FEDERALLY SPONSORED RESEARCH OR DEVELOPMENT

Not applicable.

BACKGROUND OF THE INVENTION

1. Field of the Invention

The invention relates generally to the field of measuring nuclear magnetic resonance properties of an earth formation traversed by a borehole. More particularly, the invention presents method and apparatus adapted for using in pipe assisted wireline and similar applications, including through the drill bit applications.

2. Background Art

Various prior approaches have been suggested and implemented for measuring nuclear magnetic resonance (NMR) properties of earth formations surrounding a borehole to evaluate the earth formations. Most recent generation of NMR well logging instruments employs a static magnetic field produced by a permanent magnet to align nuclear spin magnetic moments of protons or other nuclei present in the earth formations. The aligned spin magnetic moment is typically brought into excited state by applying an RF magnetic field. RF voltages are induced in the receive antenna as a result of precessional rotation of nuclear spin axes of hydrogen protons about the static magnetic field with characteristic resonance or Larmor frequency corresponding to the static magnetic field strength.

Practical wireline NMR downhole tools are represented by U.S. Pat. No. 4,717,878 issued to Taicher et al. representing a centralized type tool design, U.S. Pat. No. 5,055,787 issued to Kleinberg et al. representing a skid type side looking design with quasi-homogeneous static magnetic field, and U.S. Pat. No. 6,452,388 issued to Reiderman, et al. representing side-looking gradient type design. A permanent magnet used in all the practical wireline NMR tools generates polarizing magnetic field that aligns nuclear spin magnetic moment. The angle between the nuclear magnetization and the polarizing magnetic field is then changed by applying a pulsed radio-frequency (RF) magnetic field at a frequency corresponding to the static magnetic field magnitude at a predetermined distance from the NMR tool. A sequence of RF pulses can be designed to manipulate the nuclear magnetization in order to acquire NMR relaxation property of the earth formation. For the NMR well logging the most common sequence is the CPMG sequence that comprises one excitation pulse and a plurality of refocusing pulses. One of the main challenges of the NMR downhole measurements is to achieve an acceptable signal-to-noise ratio (SNR). Typical SNR for downhole NMR measurements is 3-10 per one measurement cycle. For the configurations of the magnets and the antennas of the NMR tools represented in the US patents '878 '787 and '388 the SNR is less for smaller tool diameter.

Pipe assisted wireline method of acquiring borehole data gives unique capability of acquiring formation data in difficult well situations, as well as in high angle or horizontal wells. This method typically require small diameter logging tools capable of being lowered or raised through the drill string. Typical tool diameter for this application is about 2 inches. There are no NMR logging tools having outer diameter small enough to be used in the pipe assisted wireline application. A prior art NMR logging tool of this diameter would have an unacceptably small SNR. Therefore there is a need for an ultra slim NMR logging tool with sufficiently high SNR.

Thus known in the art instruments do not give any satisfactory solution for an ultra-slim NMR logging tool with sufficiently high SNR. Therefore it is an objective of the present invention to provide a solution for high SNR slim NMR tool suitable for the pipe assisted wireline application.

BRIEF SUMMARY OF THE INVENTION

One aspect of the present invention is an ultra-slim NMR well logging tool that comprises a magnet to generate static magnetic field, an antenna to generate radio-frequency magnetic field in the volume of interest in the earth formations, the magnet and the antenna are adapted for lowering or raising through a drill string. The magnet and the antenna have a longitudinal axis of elongation parallel to the axis of the drill string. The magnet is magnetized in the direction perpendicular to the magnet axis. The antenna has a closed position configuration while moving the tool within the drill string. The antenna has also an open position configuration when performing measurements outside the drill string. The open position configuration of the antenna has a greater magnetic dipole moment. The greater magnetic dipole moment of the antenna enhances the NMR signal and the signal-to-noise ratio. The antenna wires in the open position configuration produce radio-frequency magnetic field which is substantially perpendicular to the static magnetic field in the volume of interest. Also, in the open position configuration the antenna wire is located farther from the magnet. This reduces magneto-acoustic ringing, which typically accompanies NMR measurements, especially in case of "inside-out" NMR sensors used in NMR well logging applications. In a preferred embodiment of the invention the magnet has a first configuration realized while moving the tool within the drill string and a second configuration realized when performing measurements outside the drill string. In the first configuration the magnet has substantially zero dipole magnetic moment and, consequently, zero magnetic field outside the magnet in order to prevent the magnet from getting stuck inside the drill pipe due to the magnetic attraction force between the magnet and the drill pipe. In the second configuration of the magnet it has maximum possible dipole moment and generate maximum possible magnetic field outside the magnet. In a preferred embodiment of the NMR tool the antenna wires are attached to a retractable bow spring centralizer which is retracted when the tool is within the drill string and expends into the borehole when the tool is in measurement position.

Another preferred embodiment of the ultra-slim NMR logging tool of the present invention is an axially symmetrical tool comprising a first soft magnetic core with a set of coils driven by a DC current to generate a radial static magnetic field in a region of interest. The region of interest has a form of elongated cylindrical shell coaxial with the tool axis. Uniformity of the static magnetic field over the volume of investigation is achieved by adjusting currents in separate coils or a current density in one coil. A second magnetic core with at least one coil is used to generate radiofrequency magnetic field in the region of interest and receive NMR signals from the region of interest, the radio-frequency magnetic field direction is substantially perpendicular to the static magnetic field. The second magnetic core is substantially electrically non-conductive.

Another aspect of the present invention is an at least one side-looking NMR sensor for acquiring fast relaxation component of the NMR signal. The sensor comprises a source of static magnetic field and a source of radio-frequency magnetic. The static magnetic field and the radio-frequency magnetic field are mutually orthogonal. Both fields are perpendicular to the borehole axis. A magnetic core made of a magnetically permeable material is used as a part of the static magnetic field source and the radio-frequency magnetic field source. The arrangement used as the radio-frequency magnetic field source can be used also as a receiver of the NMR signal. The sensor is configured as a magnetic head-type device with substantially no parasitic NMR excitation in the borehole. In one embodiment of the side-looking NMR sensor the source of the static magnetic field is a coil wound around the magnetic core. A plurality of the sensors can be used to enable azimuthal selectivity of measurements.

Yet another aspect of the present invention is a method of measuring properties of the earth formation at high logging speed or in case of relatively short excitation region in axial direction. The method comprises employing a first radio-frequency pulse sequence to generate steady state free precession of nuclear spins and acquire signal proportional to a total amount of hydrogen in porous space of the earth formations and employing a second pulse sequence that uses short trains of radio-frequency pulses and a short time interval between the trains to estimate the amount of nuclei having fast NMR relaxation. The fast relaxation amount is preferably acquired using the side-looking NMR sensor. The method further comprises estimating parameters of the porous space in the earth formations and characterizing fluids in the porous space based on the total amount of hydrogen and the amount of nuclei having fast NMR relaxation.

Other aspects and advantages of the invention will be apparent from the following description and the appended claims.

BRIEF DESCRIPTION OF THE DRAWINGS

This invention is best understood with reference to the accompanying figures in which like numerals refer to like elements.

FIGS. 4A and 4B illustrate fragments of an antenna assembly.

FIGS. 5A, 5B, 5C collectively referred to as FIG. 5 depict an exemplary embodiments of the magnet assembly. FIGS. 5A and 5B represent an embodiment with two coaxial magnets in two positions: 1) when the NMR logging tool is conveyed through the drill pipe (FIG. 5A), and 2) when performing measurements (FIG. 5B). FIG. 5C represents an embodiment with centralizing rollers.

DETAILED DESCRIPTION OF THE INVENTION

Figure 1:
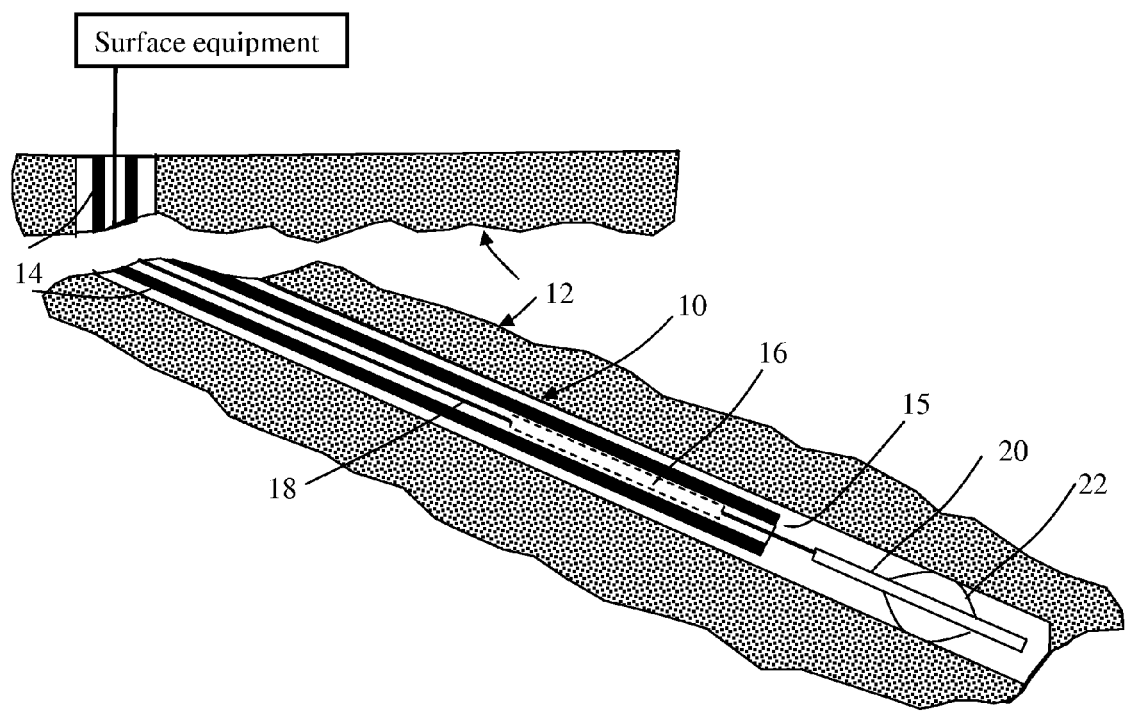
FIG. 1 illustrates an exemplary embodiment of a logging instrument used in pipe assisted wireline application.

FIG. 1 shows a borehole 10 drilled into a geological formation 12 to be investigated for potential hydrocarbon producing reservoirs. A drill string 14 extends from a drilling rig (not shown) into the borehole 10 whereby the open lower end 15 is disposed in the open lower borehole portion. An NMR logging tool 16 capable of being lowered or raised through the drill string 14 is suspended in the drill string 14 using a wireline cable 18 deployment. The tool is typically lowered down the drill string and "pumped" out of drill pipe into open hole. The NMR logging tool in the open hole position is shown at 20. The tool 20 has a retractable bow spring centralizer 22. Instead of the bow spring the tool 20 may have retractable arms or a "car jack" type centralizer. The tool 20 may be powered by a battery (not shown) and can be provided with an electronic memory (not shown) or other recording medium for storing measurement data. The simplified layout of FIG. 1 can represent both a known in the art logging tool and an embodiment of the present invention.

It is to be clearly understood that the embodiment of the logging tool shown in FIG. 1 is only an example. It is within the scope of this invention to include different modes of operation: a wireline, including through the bit conveyance (out through the pipe end or through the bit) or memory mode (hanging the tool of the pipe end or off the bit and logging while tripping pipe). In both cases the tool may be lowered on wireline, by pumping down, or combination of the two.

Figure 2:
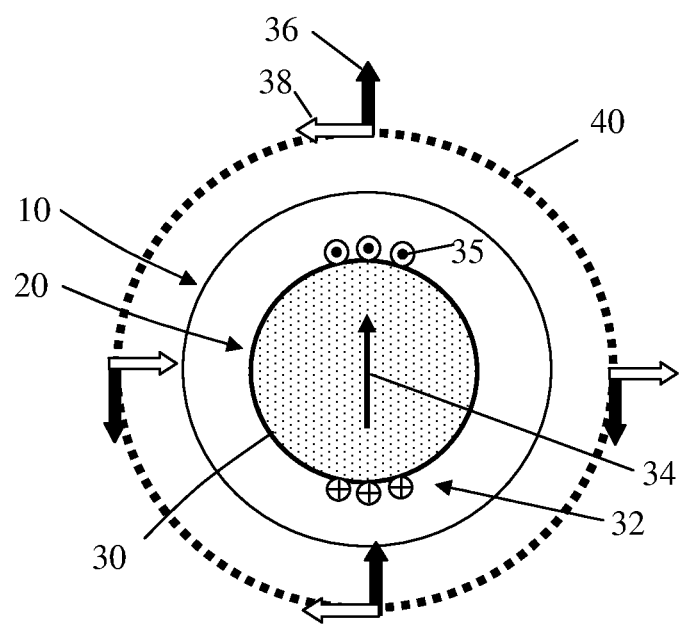
FIG. 2 shows a cross sectional view of an exemplary embodiment of a prior art magnet and RF antenna assembly used for NMR well logging measurement.

Turning now to FIG. 2, where a cross-sectional view (the plane perpendicular to the borehole axis) of the NMR logging tool of prior art is presented. The logging tool comprises a magnet 30 and the antenna 32. Magnetization direction 34 of the magnet is perpendicular to the axis of the tool, the axis is parallel to the axis of the borehole. Electrical current direction 35 is parallel to the axis of the tool (dots and the crosses show directions pointing toward and away from the viewer respectively). A static magnetic field 36 and a radio-frequency magnetic field 38 are mutually orthogonal and have a substantially constant magnitude at the volume of investigation 40.

It was shown in U.S. Pat. No. 5,712,566 that the signal-to-noise ratio for the tool configuration shown in FIG. 2 can be presented as follows (the constants are omitted):

$$SNR \propto B_0^{1/4} \cdot \left(\frac{B_1}{I_1}\right)^{3/2}, \tag{1}$$

where $B_0$ is the static magnetic field in the volume of investigation (NMR excitation volume), $$\left(\frac{B_1}{I_1}\right)$$

is the antenna efficiency defined as a radio-frequency magnetic field that would be generated in the volume of investigation by unit current in the antenna wire.

Since $B_0$ is proportional to the cross-sectional area of the magnet and $(B_1/I_1)$ is proportional to the diameter of the antenna assembly (substantially the same as the diameter of the magnet for the tool presented in FIG. 2) it is clear from the equation (1) that reducing diameter of the tool presented in FIG. 2 would drastically reduce the SNR, specifically, as the diameter squared. This means that a 2" diameter tool would have approximately 10 time less SNR than a 6" diameter tool making the 2" diameter tool impractical. This consideration is principally valid for all the practical wireline NMR tools described in the US patents '878 '787 and '388.

Figure 3A:
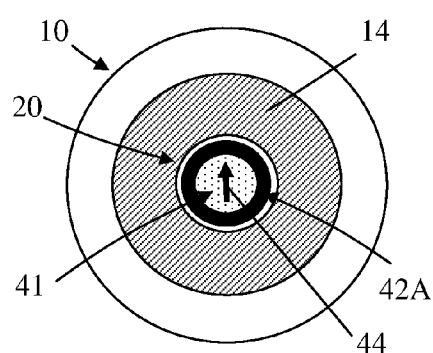
FIG. 3A, FIG. 3B and FIG. 3C, collectively referred to as FIG. 3, depict respectively a cross-sectional view of an exemplary embodiment of a logging tool in closed position as conveyed within the drill pipe, a cross-sectional view of the logging tool in open position as used when performing measurement, and a side view of the logging tool in open position.
Figure 3B:
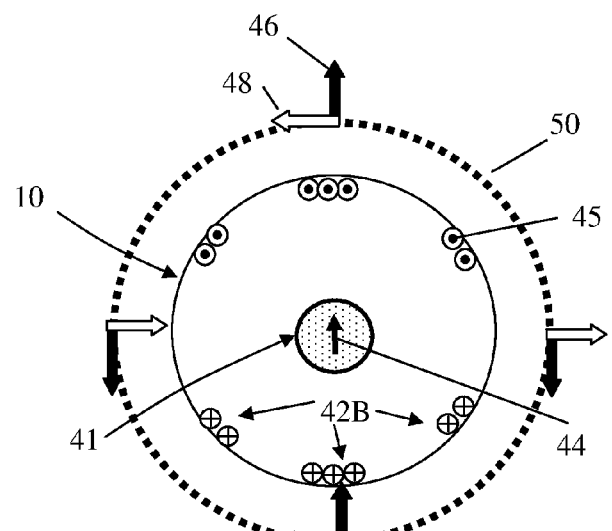
Figure 3C:
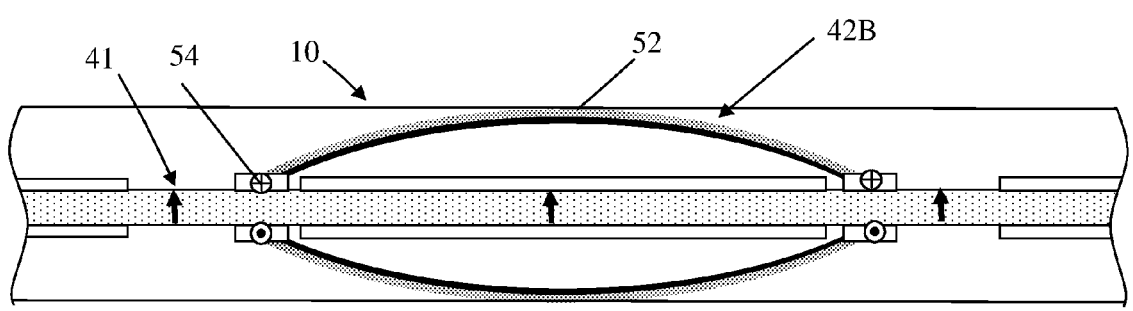

FIG. 3A, FIG. 3B and FIG. 3C represent a preferred embodiment of the present invention. FIG. 3A shows the NMR tool 20 inside the drill pipe 14 while conveying the tool through the drill pipe disposed in the borehole 10. The tool comprises a magnet 41 having magnetization direction 44 and an antenna assembly 42A. FIG. 3B and FIG. 3C show the tool when the antenna assembly is expanded radially toward the borehole wall. In order to provide a desired matching between the static magnetic field 46 and the radio-frequency magnetic field 48 the antenna current 45 is preferably distributed as shown at 42B. The distribution should preferably approximate a cos(φ) distribution, where φ is the angle between the direction of magnetization of the magnet and a direction toward a particular point on the perimeter of the antenna assembly. In a simplified arrangement of FIG. 3 the antenna current carrying wires are attached to a retractable bow spring 52. A number of bow springs can be used to accommodate antenna wires in order to provide a desired distribution of the antenna current density. The antenna currents make closed loops by running wires around the magnet as shown at 54. All antenna wires are preferably connected in series. FIG. 3C shows a cross-sectional view in the plane defined by the direction of the magnetization of the magnet and the direction of the tool axis.

In the open position configuration the antenna wire is located farther from the magnet. This reduces magneto-acoustic ringing, which typically accompanies NMR measurements, especially in case of "inside-out" NMR sensors used in NMR well logging applications.

FIG. 4 shows a fragment of the antenna assembly 42. The fragment shown in two exemplary embodiments FIG. 4A and FIG. 4B. The fragment illustrates possible layout of the antenna wires attached to one arm of the bow spring centralizer 52. In one embodiment a single flat wire 57 is attached to the spring 56. FIG. 4B presents another embodiment using a flexible printed circuit board 58 with multiple wires 59.

FIG. 5 represents possible embodiment of the magnet 41. The embodiment is intended to eliminate or reduce the attraction magnetic force between the magnet and the drill pipe (typically made of a magnetic steel) while the tool is conveyed through the interior of the drill string 14 (FIG. 1). FIG. 5A and FIG. 5B represent a magnet made of an outer 60A and inner 60B cylinders. While the tool is conveyed within the drill string 14 the relative azimuthal orientations of the cylinders is such that the total magnetic dipole of the magnet and, correspondingly, the external magnetic field is substantially zero. This state of the magnet is represented in FIG. 5A. When conducting NMR measurements in the borehole (outside the drill string) the outer and the inner cylinders have the same direction of magnetization, therefore the magnet 41 generate maximum possible static magnetic field. FIG. 5C shows an embodiment of the magnet where the magnet is centralized in the drill string bore using rollers 61. The centralized magnet has substantially zero attraction force to the drill string.

The diameter of the borehole 10 and the position of the tool with respect to the borehole axis can slightly change during logging the well. This may cause a measurement error (e.g. in a form of a parasitic random modulation of the measured NMR signal) due to change of the effective area of the antenna. One or more miniature magnetometer attached to each arm of the bow spring centralizer are preferably used to measure distances from the bow springs to the magnet 41 and make corrections for the variation of the borehole diameter and the tool position.

Figure 6:
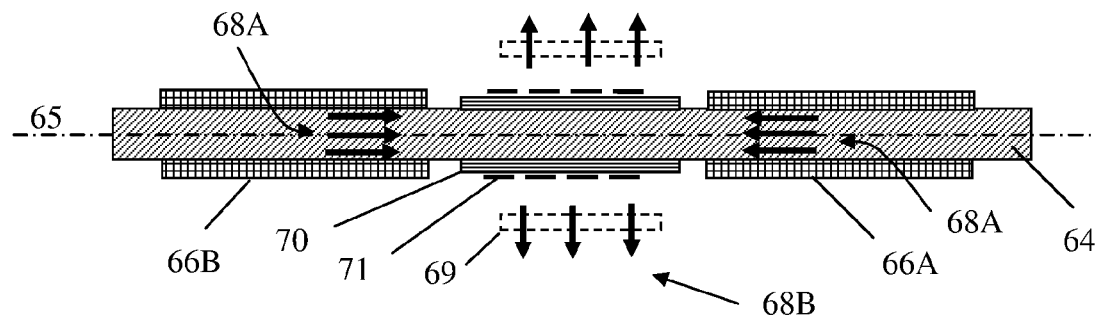
FIG. 6 illustrates an exemplary embodiment of a slim logging tool with longitudinal RF antenna.

FIG. 6 represents another embodiment of the ultra-slim NMR tool. The tool has an axial symmetry with the axis 65. The NMR tool has a first magnetic core 64 made of a high saturation flux density soft magnetic material (e.g. a low carbon steel). Two windings 66A and 66B are energized by a DC power supply (not shown in FIG. 6) and used to generate magnetic flux 68A inside the first magnetic core; the flux is directed toward the center of the first magnetic core as shown in FIG. 6. The magnetic flux comes out of the core 64 in its central region as shown at 68B to generate the static magnetic field in the volume of investigation 69. The volume of investigation 69 has a shape of a cylindrical shell. The static magnetic field has radial direction in the volume of investigation. An axial distribution of the current density in the windings and the axial position of the windings is selected to provide axial uniformity of the static magnetic field in the volume of investigation 69. A radio-frequency coil 71 and a second magnetic core 70 are used to generate a radio-frequency magnetic field in the volume of investigation. The radio-frequency magnetic field direction is substantially parallel to the a axis of the tool in the volume of investigation. The second magnetic core 70 is made of a substantially electrically non-conductive soft magnetic material (ferrite or a laminated structure made of thin metal tapes or ribbons that is a macroscopically non-conductive structure). The second magnetic core is used to concentrate the radio-frequency magnetic flux. It also acts as a magnetic shield between the coil 71 and the electrically conductive first magnetic core 64. Without the shield the radio-frequency coil quality factor and the radio-frequency dipole moment would be significantly reduced by the presence of the first magnetic core 64. It would be readily understood by those skilled in the art that a reduction of the diameter of the tool and, consequently, the diameter of the second magnetic core 70 and the coil 71 will have substantially no effect on the efficiency of generation of the radio-frequency magnetic field in the volume of interest. This is due to the fact that the radio-frequency magnetic dipole is mainly determined by the magnetic flux generated in the magnetic core 70 and also by the fact that the decrease of the diameter of the core would equally reduce the cross-sectional area of the core and increase its effective magnetic permeability (the latter is primarily determined by the elongation ratio of the core rather than the magnetic permeability of the material used to make the core).

While the tool is conveyed through the interior of the drill string 14 (FIG. 1) the windings 66A and 66B are not energized, therefore there is no attraction magnetic force between the magnet and the drill pipe during the tool conveyance process.

Figure 7:
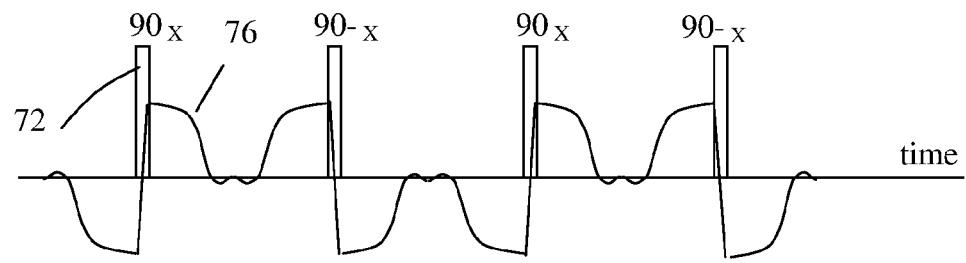
FIG. 7 depicts an exemplary RF pulse sequence to be preferably used with the embodiment of the slim tool presented in FIG. 6.

Reference is now made to FIG. 7 where a method of measuring properties of the earth formation at high logging speed or in case of relatively short excitation region extent in axial direction. The method comprises employing a first radiofrequency pulse sequence to generate steady state free precession (SSFP) of nuclear spins (described, for example, in P. Mansfield and P.G. Morris. NMR Imaging in Biomedicine) and acquire signal proportional to a total amount of hydrogen in porous space of the earth formations. An exemplary SSFP pulse sequence comprises phase alternated 90° radio-frequency pulses 72 (shown in the FIG. 7 are the envelopes of the radio-frequency pulses). The SSFP nuclear magnetization response is shown at 76. The response 76 is the nuclear magnetization (the envelopes of the radio-frequency magnetization patterns) in the plane perpendicular to the static magnetic field direction. The method also employs a second pulse sequence that uses short trains of the radio-frequency pulses and a short time interval between the trains to estimate the amount of nuclei having a fast NMR relaxation. The fast relaxation components of the nuclear magnetization is preferably acquired using the side-looking NMR sensor described later herein. The method further comprises estimating parameters of the porous space in the earth formations and characterizing fluids in the porous space based on the total amount of hydrogen nuclei and the amount of nuclei having fast NMR relaxation.

Figure 8A:
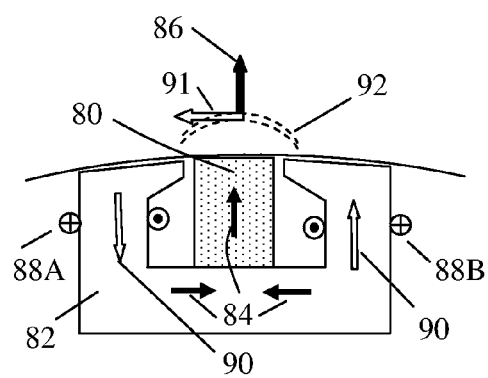
FIG. 8A, FIG. 8B and FIG. 8C illustrates an exemplary embodiment of an auxiliary magnet and antenna assemblies (side-looking NMR sensors) for high resolution measurement of fast components of NMR relaxation.
Figure 8B:
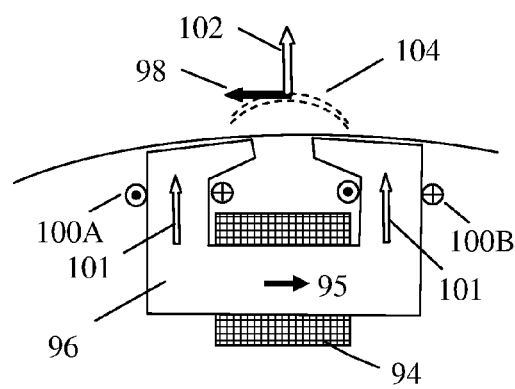
Figure 8C:
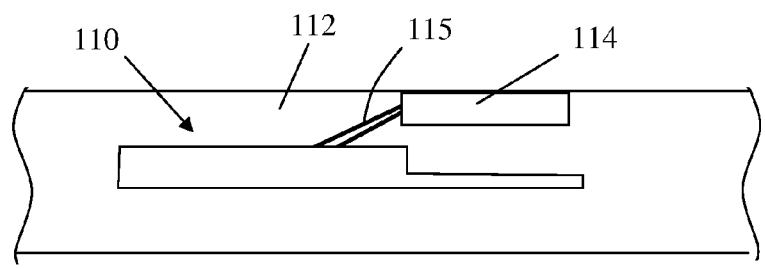

FIG. 8A, FIG. 8B, and FIG. 8C represent another aspect of the present invention: a side-looking NMR sensor for acquiring fast relaxation component of the NMR signal. In one embodiment of the sensor shown in FIG. 8A the sensor comprises a source of local static magnetic field represented by a magnet 80 and a soft magnetic core 82. The magnetic flux of the magnet and the static magnetic flux in the core is shown at 84. The magnetic flux and the magnetic field 86 in the volume of investigation 92 in the earth formations is directed perpendicular to the borehole axis (not shown in FIG. 8A). The borehole axis is perpendicular to the plane of the drawing. A radio-frequency magnetic flux in the core is generated by the radiofrequency coil, the two parts of which are shown at 88A and 88B. The radio-frequency magnetic flux direction in the core is shown at 90. The radio-frequency magnetic field 91 at the volume of interest is perpendicular to the direction of the static magnetic field and also perpendicular to the borehole axis (the latter is perpendicular to the plane of the drawing). The soft magnetic core made of a magnetically permeable material is used as a part of the static magnetic field source and as a part of the radio-frequency magnetic field source. In another embodiment of the side-looking sensor shown in FIG. 8B the source of the static magnetic field is formed by a coil 94 and a magnetic core 96. The static magnetic flux direction in the magnetic core is shown at 95. The static magnetic field direction in the volume of interest 104 is shown at 98. A radio-frequency magnetic flux in the core is generated by the radiofrequency coil, the two parts of which are shown at 100A and 100B. The radio-frequency magnetic flux direction in the core is shown at 101. The radio-frequency magnetic field 102 at the volume of interest is perpendicular to the direction of the static magnetic field and also perpendicular to the borehole axis (the latter is perpendicular to the plane of the drawing). In both embodiment of the side-looking sensor presented in FIG. 8 the radio-frequency coils can be used for generating the radiofrequency magnetic field in the volume of interest and also to receive nuclear magnetization signal emanating from the volume of interest. FIG. 8C shows a side view of the side-looking sensors. Shown at 110 is a part of the logging tool in the borehole 112 after passing through the interior of the drill string. The side-looking sensor 114 is attached to the tool using a retractable arm 115.

In both embodiment of the side-looking sensor presented in FIG. 8 the soft magnetic core is made of a magnetically permeable material that is macroscopically non-conductive (ferrite or stack of thin soft magnetic metal ribbons or tapes separated by insulating layers). The core is used as part of the static magnetic field generation, the radio-frequency magnetic field generation and the nuclear magnetization signal reception subsystems of the sensor. In both embodiments of the side-looking sensor presented in FIG. 8 the radio-frequency coils can be used for generating the radiofrequency magnetic field in the volume of interest and also to receive signals produced by X-Y components of the nuclear magnetization It is important that the sensors presented in FIG. 8 are configured as a magnetic head-type device with substantially no parasitic NMR excitation in the borehole.

A plurality of the sensors can be used to enable measurements in different directions (azimuthal selectivity of measurements).

It would be readily understood by those skilled in the art that in the embodiments of the ultra-slim logging tool and the side-looking sensors presented in FIG. 3, FIG. 6, and FIG. 8 separate coils can be used for transmission and reception of NMR signals from the volume of interest.

It would be also understood by those skilled in the art that the antenna wires (see a preferred embodiment in FIG. 3) placed on different arms of the bow spring centralizer could be connected to different receivers in order to enable directional measurement (an azimuthal selectivity).

While the invention has been described with respect to a limited number of embodiments, those skilled in the art, having benefits of this disclosure, will appreciate that other embodiments can be devised which do not depart from the scope of invention as disclosed herein. For example, to facilitate high signal-to-noise NMR measurements in a range of borehole diameters (e.g. from 6 inches to 17 inches range) an embodiment of a conventional wireline conveyance NMR logging tool can be devised, which uses a slim magnet assembly and a larger diameter antenna assembly as shown in FIG. 3B and FIG. 3C. Bow springs or retractable arms can be used to make the antenna assembly adjustable to expand radially toward the borehole wall and therefore providing a sufficiently large magnetic dipole moment of the NMR antenna.

What I claim as my invention is:

1. An apparatus for measuring nuclear magnetic resonance properties of earth formations surrounding a borehole, comprising:
    a logging device movable through the borehole;
    a drill string for lowering and raising the logging device in the borehole, wherein the drill string is configured for passing the logging device from a position within the drill string to a position outside the drill string at a lower end part thereof, the nuclear magnetic resonance properties being measured when the logging device is suspended in the position outside the drill string;
    a magnet assembly in the logging device to generate a static magnetic field;
    an antenna assembly in the logging device for at least one of generating a radio-frequency magnetic field and receiving nuclear magnetic resonance signals, the antenna assembly being adjustable to expand toward the borehole wall, wherein the antenna assembly has a closed configuration when the logging device is in the position within the drill string and an open configuration when measuring the nuclear magnetic resonance properties in the position outside the drill string, the antenna assembly having a greater antenna magnetic dipole moment in the open configuration; and a receiver for processing the nuclear magnetic resonance signals.

2. The apparatus of claim 1 wherein the magnet assembly has an axis of elongation, and the static magnetic field is perpendicular to the axis of elongation.

3. The apparatus of claim 1, wherein the drill string is provided with a drill bit at the lower end of the drill string, the logging device being capable of passing through the drill bit to the outside position for measuring the nuclear magnetic resonance properties.

4. The apparatus of claim 1 wherein the magnet assembly comprises a set of rollers to reduce friction between the magnet assembly and the drill string interior surface.

5. The apparatus of claim 1 wherein the antenna assembly in the open configuration takes a farthermost position from the magnet assembly to enable at least one of increase of the antenna magnetic dipole moment and reduction of magneto-acoustic ringing.

6. The apparatus of claim 1 wherein the antenna assembly comprises an at least one wire attached to a centralizer.

7. The apparatus of claim 6 wherein the centralizer comprises one of a bow spring and an arm to centralize the magnet assembly in the borehole.

8. The apparatus of claim 1 wherein the antenna assembly comprises an at least one wire attached to a retractable centralizer, wherein the retractable centralizer is retracted when passing the logging device within the drill string and centralize the magnet assembly in the borehole when measuring the nuclear magnetic resonance properties.

9. The apparatus of claim 8 wherein the retractable centralizer comprises one of a retractable bow spring centralizer and a retractable arm centralizer.

10. The apparatus of claim 1 wherein the antenna assembly comprises multiple conductors configured to expand radially toward the borehole wall to produce a desired distribution of the radio-frequency magnetic field in the earth formations surrounding the borehole.

11. The apparatus of claim 1 wherein the antenna assembly comprises multiple conductors, each of the multiple conductors connected to a separate circuitry and the receiver is configured to estimate an azimuthal distribution of the nuclear magnetic resonance properties of the earth formations surrounding the borehole.

12. The apparatus of claim 1 wherein the logging device further comprises a side-looking sensing assembly having higher operating frequency, the side-looking sensing assembly configured to acquire fast relaxation components of the nuclear magnetic resonance signals, wherein the receiver is configured to process the nuclear magnetic resonance signals received by the antenna assembly and the magnetic resonance signals received by the side-looking sensing assembly to evaluate the earth formations surrounding the borehole.

13. An apparatus for measuring nuclear magnetic resonance properties of earth formations surrounding a borehole, comprising:

a logging device movable through the borehole;

a drill string for lowering and raising the logging device in the borehole, wherein the drill string is configured for passing the logging device from a position within the drill string to a position outside the drill string at a lower end part thereof, the nuclear magnetic resonance properties being measured when the logging device is suspended in the position outside the drill string;

a magnet assembly in the logging device to generate a static magnetic field;

an antenna assembly in the logging device for at least one of generating a radio-frequency magnetic field and receiving nuclear magnetic resonance signals, wherein the magnet assembly has a first configuration when the logging device is in the position within the drill string and a second configuration when measuring the nuclear magnetic resonance properties in the position outside the drill string, the first configuration of the magnet assembly having a substantially zero dipole magnetic moment to substantially eliminate a magnetic attraction force between the magnet assembly and the drill string.

14. A method for measuring nuclear magnetic resonance properties of earth formations surrounding a borehole, comprising:

conveying a logging device in the borehole, wherein conveying the logging device includes passing the logging device through a drill string from a position within the drill string to a position outside the drill string at a lower end part thereof, the nuclear magnetic resonance properties being measured when the logging device is suspended in the position outside the drill string;

using a magnet assembly to generate a static magnetic field in the earth formations, wherein using the magnet assembly includes reconfiguring the magnet assembly from an arrangement with substantially zero magnetic dipole moment when the logging device is in the position inside the drill string to an arrangement with maximum dipole moment when the logging device is in the position outside the drill string; and using an antenna assembly in the logging device for at least one of generating a radio-frequency magnetic field in the earth formations and receiving nuclear magnetic resonance signals, the antenna assembly being adjustable to expand radially toward the borehole wall to increase a magnetic dipole moment of the antenna assembly.

15. The method of claim 14 wherein the step of using an antenna assembly further comprises adapting the antenna assembly to have a plurality of current loops to generate a substantially axisymmetrical distribution of magnitude of the radio-frequency magnetic field in the earth formations surrounding the borehole, the radio-frequency magnetic field being substantially perpendicular to the static magnetic field in the earth formations surrounding the borehole to satisfy nuclear magnetic resonance excitation conditions.

16. The method of claim 14 wherein the step of using an antenna assembly further comprises using a magnetometer to measure a distance from a fragment of the antenna assembly to the magnet assembly and make corrections for the variation of the borehole diameter and the logging device position.

* * * * *